(12) United States Patent
Santarpia, III et al.

(10) Patent No.: US 9,526,681 B2
(45) Date of Patent: Dec. 27, 2016

(54) COMPOSITIONS AND METHODS FOR TREATING DENTAL CARIES

(71) Applicant: Colgate-Palmolive Company, New York, NY (US)

(72) Inventors: Ralph Peter Santarpia, III, Edison, NJ (US); Iraklis Pappas, Pennsauken, NJ (US); Elizabeth Gittins, Stewartsville, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/649,136

(22) PCT Filed: Dec. 3, 2012

(86) PCT No.: PCT/US2012/067547
§ 371 (c)(1),
(2) Date: Jun. 2, 2015

(87) PCT Pub. No.: WO2014/088535
PCT Pub. Date: Jun. 12, 2014

(65) Prior Publication Data
US 2015/0335551 A1 Nov. 26, 2015

(51) Int. Cl.
A61K 8/44 (2006.01)
A61K 8/97 (2006.01)
A61Q 11/00 (2006.01)
A61K 8/19 (2006.01)
A61K 8/34 (2006.01)
A61K 8/55 (2006.01)

(52) U.S. Cl.
CPC . *A61K 8/34* (2013.01); *A61K 8/19* (2013.01); *A61K 8/44* (2013.01); *A61K 8/55* (2013.01); *A61Q 11/00* (2013.01); *A61K 2800/28* (2013.01)

(58) Field of Classification Search
USPC ..................................... 424/49, 57, 401, 58
See application file for complete search history.

(56) References Cited

U.S. PATENT DOCUMENTS

| | | |
|---|---|---|
| 3,535,421 A | 10/1970 | Briner et al. |
| 3,538,230 A | 11/1970 | Pader et al. |
| 3,678,154 A | 7/1972 | Widder et al. |
| 3,862,307 A | 1/1975 | Di Giulio |
| 3,937,807 A | 2/1976 | Haefele |
| 3,959,458 A | 5/1976 | Agricola et al. |
| 4,051,234 A | 9/1977 | Gieske et al. |
| 4,340,583 A | 7/1982 | Wason |
| 4,842,847 A | 6/1989 | Amjad |
| 4,866,161 A | 9/1989 | Sikes et al. |
| 4,885,155 A | 12/1989 | Parran, Jr. et al. |
| 5,004,597 A | 4/1991 | Majeti et al. |
| 5,116,602 A | 5/1992 | Robinson et al. |
| 5,256,401 A | 10/1993 | Duckenfield et al. |
| 5,424,059 A | 6/1995 | Prencipe et al. |
| 6,214,320 B1 | 4/2001 | Gaffar et al. |
| 6,361,787 B1 | 3/2002 | Shaheen et al. |
| 7,048,910 B2 | 5/2006 | Buenger et al. |
| 7,871,649 B2 | 1/2011 | Modak et al. |
| 8,173,182 B2 | 5/2012 | Van Beek |
| 8,906,349 B2 | 12/2014 | Schaeffer-Korbylo et al. |
| 2005/0281521 A1 | 12/2005 | Oku et al. |
| 2006/0002671 A1 | 1/2006 | Oku et al. |
| 2009/0202450 A1 | 8/2009 | Prencipe et al. |
| 2009/0202451 A1 | 8/2009 | Prencipe et al. |
| 2009/0202454 A1 | 8/2009 | Prencipe et al. |
| 2009/0202455 A1 | 8/2009 | Kohli et al. |
| 2010/0316580 A1 | 12/2010 | Kohli et al. |
| 2010/0330002 A1 | 12/2010 | Robinson et al. |
| 2010/0330003 A1 | 12/2010 | Robinson et al. |
| 2011/0014136 A1 | 1/2011 | Kohli et al. |
| 2012/0128599 A1 | 5/2012 | Schaeffer-Korbylo et al. |
| 2013/0323185 A1 | 12/2013 | Lavender et al. |

FOREIGN PATENT DOCUMENTS

| | | | |
|---|---|---|---|
| DE | 19506706 | | 8/1996 |
| EP | 0348560 | | 1/1990 |
| JP | S58-213706 | | 12/1983 |
| JP | H08151324 | | 6/1996 |
| JP | H08151326 | | 6/1996 |
| WO | WO2009099455 | | 8/2009 |
| WO | WO 2011/019342 | * | 2/2011 |
| WO | WO2011043397 | | 4/2011 |
| WO | WO 2012/001337 | | 1/2012 |

OTHER PUBLICATIONS

Hiramoto et al., 2011, "Agent used in fragrance composition, food and drink, cosmetics, daily use products and pharmaceutical formulation for treating influenza virus infection, comprises patchouli alcohol and/or patchouli essential oil extract," Database WPI Thomson AN: 2011-D85968 & JP 2011-079800.

International Search Report and Written Opinion in International Application No. PCT/US2012/067547, mailed Aug. 9, 2013.

(Continued)

*Primary Examiner* — Lezah Roberts

(57) ABSTRACT

Described herein are oral compositions comprising a basic amino acid, in free or salt form, and a sesquiterpene alcohol; and methods of making and using the same.

21 Claims, No Drawings

(56) References Cited

OTHER PUBLICATIONS

Kayser et al., 1998, "Composition of the essential oils of Pelargonium sidoiles DC. and Pelargonium reniforme Curt.," Flavour and Fragrance Journal 13:209-212.
Suidouh, 1996, "Antimicrobial composition preferably for oral use—consists of arginine or its derivative antibacterial compound and nonionic or amphoteric surfactant," Database WPI Thomson AN: 1996-329423 & JP H08-151324.
Suidouh, 1996, "Antimicrobial preparation for treating dental caries and stomatitis etc.—comprises histidine, antimicrobial compound and nonionic surfactant," Database WPI Thomson AN: 1996-329425 & JP H08-151326.
Written Opinion in International Application No. PCT/US2012/067547, mailed Oct. 31, 2014.

* cited by examiner

COMPOSITIONS AND METHODS FOR TREATING DENTAL CARIES

BACKGROUND

Dental caries are exemplified by demineralization and deterioration of hard dental structures and tissues, including enamel, dentin and cementum. The major cause of dental caries is production of acid by bacterial fermentation of food debris accumulated on the tooth surface. It is understood that the frequency of which teeth are exposed to acidic environments (low pH) affects the likelihood of caries development.

Thus, there remains a need for oral care compositions that are effective in maintaining the appropriate pH in the oral cavity and reducing the occurrence and/or progression of dental caries. Embodiments of the present invention are directed to these ends.

SUMMARY

Some embodiments, of the present invention are directed to oral care compositions comprising a basic amino acid, in free or salt form, and a sesquiterpene alcohol. Other embodiments of the present invention are directed to methods of treating or preventing dental caries, using the compositions described herein.

DETAILED DESCRIPTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

Some embodiments of the present invention are directed to oral care compositions comprising a sesquiterpene alcohol and a basic amino acid, in free or salt form. In some embodiments, the sesquiterpene alcohol comprises a monocyclic sesquiterpene alcohol. In some embodiments, the monocyclic sesquiterpene alcohol comprises bisabolol. In some embodiments, the monocyclic sesquiterpene alcohol comprises α-(−)-bisabolol. In some embodiments, the monocyclic sesquiterpene alcohol comprises a mixture of α-(−)-bisabolol and α-(+)-bisabolol. In some embodiments, the basic amino acid is arginine. In some embodiments, the arginine is L-arginine.

In some embodiments, the sesquiterpene alcohol is bisabolol and the amino acid is arginine. In some embodiments, the bisabolol and arginine are present in a ratio between 1:2 and 2:1 bisabolol to arginine w/w.

In some embodiments, the total concentration of the combination of the sesquiterpene alcohol and the basic amino acid is 1% by weight or less.

In some embodiments, the composition is in a form selected from a paste, a gum, a liquid (e.g. a mouthwash) and a gel.

Some embodiments of the present invention provide a method of treating or preventing dental caries, comprising administering any one of the compositions described herein to the oral cavity of a subject in need thereof.

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of about 7 or greater.

Accordingly, basic amino acids include, but are not limited to, arginine, lysine, citrulline, ornithine, creatine, histidine, diaminobutanoic acid, diaminoproprionic acid, salts thereof or combinations thereof. In a particular embodiment, the basic amino acids are selected from arginine, citrulline, and ornithine.

In certain embodiments, the basic amino acid is arginine, for example, l-arginine, or a salt thereof.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In various embodiments, the basic amino acid is present in an amount of about 0.5 wt. % to about 20 wt. % of the total composition weight, about 1 wt. % to about 10 wt. % of the total composition weight, for example about 1.5 wt. %, about 3.75 wt. %, about 5 wt. %, or about 7.5 wt. % of the total composition weight.

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference.

Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

In certain embodiments, the oral care composition of the invention may also contain a source of fluoride ions or fluorine-providing ingredient in amounts sufficient to supply about 25 ppm to about 5,000 ppm of fluoride ions, generally at least about 500 ppm, e.g., about 500 to about 2000 ppm, e.g., about 1000-about 1600 ppm, e.g., about 1450 ppm.

Fluoride ion sources may be added to the compositions of the invention at a level of about 0.01 wt. % to about 10 wt.

% in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Where the composition comprises calcium bicarbonate, sodium monofluorophosphate is preferred to sodium fluoride for stability reasons.

Some embodiments of the present invention provide oral care compositions further comprise a physiologically acceptable potassium salt in an amount effective to reduce dentinal sensitivity. In some embodiments, the potassium salt is selected from potassium nitrate and potassium chloride.

The Compositions of the Invention may comprise a precipitated calcium carbonate (PCC) abrasive, calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal).

The compositions may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The abrasive polishing materials useful herein, generally have an average particle size of about 0.1 and about 30 microns, about 5 and about 15 microns. Silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, abrasive materials useful in the practice of the oral care compositions in accordance with the invention include silica gels and precipitated amorphous silica having an oil absorption value of about less than 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns.

In particular embodiments, the abrasive materials comprise very small particles, e.g., having a d50 less than about 5 microns. For example small particle silica (SPS) having a d50 of about 3-about 4 microns, for example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 5 to about 25% small particles e.g., SPS and about 10 to about 30% of a conventional abrasive.

Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of about 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

The oral care compositions of the invention also may include an agent to increase the amount of foam that is produced when the oral cavity is brushed.

Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide.

The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Another agent optionally included in the oral care composition of the invention is a surfactant or a mixture of compatible surfactants. Suitable surfactants are those which are reasonably stable throughout a wide pH range, for example, anionic, cationic, nonionic or zwitterionic surfactants.

Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference.

In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing about 8 to about 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof.

Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains about 8 to about 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

In a particular embodiment, the Composition of the Invention comprises an anionic surfactant, e.g., sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of about 0.1 to about 5% by weight and about 0.5 to about 1.5% by weight. The dosage of flavoring agent in the individual oral care composition dosage (i.e., a single dose) is about 0.001 to about 0.05% by weight and in another embodiment about 0.005 to about 0.015% by weight.

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1.0 wt. % pyrophosphate ions, about 1.5 wt. % to about 6 wt. %, about 3.5 wt. % to about 6 wt. % of such ions.

The oral care compositions of the invention also optionally include one or more polymers, such as polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Water may also be present in the oral compositions of the invention. Water, employed in the preparation of commercial oral compositions should be deionized and free of organic impurities. Water commonly makes up the balance of the compositions and includes about 10% to about 90%, about 20% to about 60% or about 10% to about 30% by weight of the oral compositions. This amount of water includes the free water which is added plus that amount which is introduced with other materials such as with sorbitol or any components of the invention.

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition.

Suitable humectants include edible polyhydric alcohols such as glycerine, sorbitol, xylitol, propylene glycol as well as other polyols and mixtures of these humectants. Mixtures of glycerin and sorbitol may be used in certain embodiments as the humectant component of the toothpaste compositions herein.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

The compositions and methods according to the invention are useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit pre-carious lesions of the enamel, e.g., as detected by quantitative light-induced fluorescence (QLF) or electronic caries monitor (ECM).

Quantitative Light-induced Fluorescence is a visible light fluorescence that can detect early lesions and longitudinally monitor the progression or regression. Normal teeth fluoresce in visible light; demineralized teeth do not or do so only to a lesser degree. The area of demineralization can be quantified and its progress monitored. Blue laser light is used to make the teeth auto fluoresce. Areas that have lost mineral have lower fluorescence and appear darker in comparison to a sound tooth surface. Software is used to quantify the fluorescence from a white spot or the area/volume associated with the lesion. Generally, subjects with existing white spot lesions are recruited as panelists. The measurements are performed in vivo with real teeth. The lesion area/volume is measured at the beginning of the clinical. The reduction (improvement) in lesion area/volume is measured at the end of 6 months of product use. The data is often reported as a percent improvement versus baseline.

Electrical Caries Monitoring is a technique used to measure mineral content of the tooth based on electrical resistance. Electrical conductance measurement exploits the fact that the fluid-filled tubules exposed upon demineralization and erosion of the enamel conduct electricity. As a tooth loses mineral, it becomes less resistive to electrical current due to increased porosity. An increase in the conductance of the patient's teeth therefore may indicate demineralization. Generally, studies are conducted of root surfaces with an existing lesion. The measurements are performed in vivo with real teeth. Changes in electrical resistance before and after 6 month treatments are made. In addition, a classical caries score for root surfaces is made using a tactile probe. The hardness is classified on a three point scale: hard, leathery, or soft. In this type of study, typically the results are reported as electrical resistance (higher number is better) for the ECM measurements and an improvement in hardness of the lesion based on the tactile probe score.

The Compositions of the Invention are thus useful in a method to reduce pre-carious lesions of the enamel (as measured by QLF or ECM) relative to a composition lacking effective amounts of fluorine and/or arginine.

The Compositions of the invention are additionally useful in methods to reduce harmful bacteria in the oral cavity, for example methods to reduce or inhibit gingivitis, reduce levels of acid producing bacteria, to increase relative levels of arginolytic bacteria, inhibit microbial biofilm formation in the oral cavity, raise and/or maintain plaque pH at levels of at least pH 5.5 following sugar challenge, reduce plaque accumulation, and/or clean the teeth and oral cavity.

Finally, by increasing the pH in the mouth and discouraging pathogenic bacteria, the Compositions of the Invention are useful to promote healing of sores or cuts in the mouth.

Enhancing oral health also provides benefits in systemic health, as the oral tissues can be gateways for systemic infections. Good oral health is associated with systemic health, including cardiovascular health. The compositions and methods of the invention provide particular benefits because basic amino acids, especially arginine, are sources of nitrogen which supply NO synthesis pathways and thus enhance microcirculation in the oral tissues. Providing a less acidic oral environment is also helpful in reducing gastric distress and creates an environment less favorable to Heliobacter, which is associated with gastric ulcers. Arginine in particular is required for high expression of specific immune cell receptors, for example T-cell receptors, so that arginine can enhance an effective immune response. The compositions and methods of the invention are thus useful to enhance systemic health, including cardiovascular health.

In some embodiments of the invention, the oral care composition includes a mixture of bisabolol and arginine. Bisabolol herein refers to α-(−)-bisabolol, α-(+)-bisabolol and/or mixtures thereof. Bisabolol, herein, also refers to a less common form of bisabolol known as β-bisabolol, which only differs from α-bisabolol by the position of the alcohol functional group.

In further embodiments, an oral care composition is made by forming a mixture of a sesquiterpene alcohol and a basic amino acid and combining them with a suitable carrier.

In some embodiments, the oral care composition is applied to teeth and gums within the oral cavity using a toothbrush, an electric brush, and irrigation system, gel strips or any other suitable means of delivery. Then after a period of time, at least a portion of the oral care composition is rinsed away from the oral cavity using, for example, water.

Compositions of the present invention can be manufactured according to various methods known in the oral care field.

Some embodiments of the present invention provide methods for making the oral care compositions described herein. In some embodiments, these methods comprise: a) forming a mixture of a sesquiterpene alcohol and a basic amino acid; and b) combining the mixture of the sesquiterpene alcohol and the basic amino acid with a carrier.

Some embodiments of the present invention provide methods of treating or preventing dental caries within an oral cavity comprising: a) applying an oral care composition to teeth within the oral cavity, wherein the oral care composition includes a mixture of a sesquiterpene alcohol and an amino acid and a carrier that includes one or more of a paste, a gum, a liquid and a gel; and b) removing a portion of the oral care composition from the oral cavity with a rinse, wherein the oral care composition reduces the pH within the oral cavity to control the dental caries.

Some embodiments provide a method comprising applying an effective amount of the oral care composition as described herein to the oral cavity of a subject in need thereof to reduce, repair or inhibit pre-carious lesions of the enamel, reduce or inhibit demineralization and promote remineralization of the teeth, reduce hypersensitivity of the teeth, reduce or inhibit gingivitis, promote healing of sores or cuts in the mouth, reduce levels of acid producing bacteria, increase relative levels of arginolytic bacteria, inhibit microbial biofilm formation in the oral cavity, raise and/or maintain plaque pH at levels of at least pH 5.5 following sugar challenge, reduce plaque accumulation, treat, relieve or reduce dry mouth, clean the teeth and oral cavity reduce erosion, immunize the teeth against cariogenic bacteria; and/or promote systemic health, including cardiovascular health.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

In order to investigate the effects of arginine alone, mixtures of arginine and bisabolol and bisabolol alone, on the production of ammonia in the present or oral bacterium the following procedures are carried out. Stimulated whole saliva is collected on ice and centrifuged for 15 minutes at 4000 rpm to obtain a pellet and salivary supernatant. The pellet, which is termed the salivary sediment, contains a representative array of the oral microbes found in the oral cavity. This pellet is washed twice in cold filter sterilized deionized water by centrifugation for 10 minutes at 4000 rpm.

The salivary sediment is then diluted to 50% with cold filter sterilized deionized water. Stock solutions of 1% arginine and 1% sucrose in filter sterilized deionized water are made, and a stock solution of 1% bisabolol in ethanol is also made. Reaction mixtures tested contain 16.7% final concentration salivary sediment, 0.1% final concentration sucrose and 0.0871% final concentration arginine. The control reaction mixture contains only salivary sediment, sucrose and arginine in the salivary supernatant base. The test solutions have a final concentration of 0.05 and 0.1 bisabolol, respectively. The reaction mixtures are then incubated at 37 degrees Celsius for 30 minutes with mild agitation before determining ammonia production. A standard diagnostic ammonia assay kit is used to quantify ammonia produced.

Table 1 (below) describes the results of the procedures described above, wherein the ammonia production is measured in terms of nanomole per milligram (nm/mg).

TABLE 1

| | A<br>Arginine<br>(Control) | B<br>0.05%<br>Bisabolol +<br>Arginine | C<br>0.05%<br>Bisabolol | D<br>0.1%<br>Bisabolol +<br>Arginine | E<br>0.1%<br>Bisabolol |
| --- | --- | --- | --- | --- | --- |
| Trial 1 (nm/mg) | 1532.40 | 2106.36 | 200.61 | 2028.34 | 133.74 |
| Trial 2 (nm/mg) | 1799.88 | 2524.28 | 27.86 | 3298.84 | 562.81 |
| Trial 3 (nm/mg) | 986.31 | 1861.17 | 66.87 | 2658.02 | 228.47 |
| Mean (nm/mg) | 1439.53 | 2163.94 | 98.45 | 2661.74 | 308.34 |

Column A in Table 1 describes data collected for three trials of L-arginine (Control) reaction mixtures that contain salivary sediment and salivary supernatant with final concentrations of 0.1% sucrose and 0.0871% L-arginine. Column B in Table 1 describes data collected for three trials of 0.05% bisabolol plus arginine reaction mixtures that contain salivary sediment and salivary supernatant with final concentrations of 0.1% sucrose, 0.05% bisabolol and 0.0871% L-arginine. Column C in Table 1 describes data collected for three trials of 0.05% bisabolol reaction mixtures that contain salivary sediment and salivary supernatant with final concentrations of 0.1% sucrose and 0.05% bisabolol. Column D in Table 1 describes data collected for three trials of 0.1% bisabolol plus arginine reaction mixtures that contain salivary sediment and salivary supernatant with final concentrations of 0.1% sucrose, 0.1% Bisabolol and 0.0871% L-arginine. Column E in Table 1 describes data collected for three trials of 0.1% bisabolol reaction mixtures that contain salivary sediment and salivary supernatant with final concentrations of 0.1% sucrose and 0.1% bisabolol.

The data described in Table 1 demonstrates that the combination of a basic amino acid (e.g. arginine) and a sesquiterpene alcohol (e.g. bisabolol) provides a synergistic increase in ammonia production from oral cavity bacteria.

What is claimed is:

1. An oral care composition comprising a monocyclic sesquiterpene alcohol and a basic amino acid, in free or salt form, wherein the monocyclic sesquiterpene alcohol is present at a concentration of from about 0.01 to about 0.5%, and wherein the sesquiterpene alcohol comprises bisabolol;
   wherein the basic amino acid is arginine, in free or salt form, and
   wherein the bisabolol and arginine are present in a ratio between 1:2 and 2:1 bisabolol to arginine w/w.

2. The composition of claim 1, wherein the monocyclic sesquiterpene alcohol comprises α-(−)-bisabolol.

3. The composition of claim 1, wherein the monocyclic sesquiterpene alcohol comprises a mixture of α-(−)-bisabolol and α-(+)-bisabolol.

4. The composition of claim 1, wherein the arginine is selected from L-arginine, arginine bicarbonate, arginine phosphate and a combination of two or more thereof.

5. The composition of claim 1, wherein the composition is in a form selected from a paste, a gum, a liquid and a gel.

6. The composition of claim 1, further comprising an abrasive.

7. The composition of claim 6, wherein the abrasive is selected from: silica; alumina; calcium pyrophosphate; calcium carbonate; and dicalcium phosphate.

8. The composition of claim 6, wherein the abrasive is selected from calcium carbonate and dicalcium phosphate.

9. The composition of claim 6, wherein the abrasive is calcium carbonate.

10. The composition of claim 9 wherein the calcium carbonate is selected from natural calcium carbonate and precipitated calcium carbonate.

11. The composition of claim 1, further comprising a pH modifying agent.

12. The composition of claim 11, wherein the pH modifying agent comprises sodium bicarbonate.

13. The composition of claim 1, comprising a small particle fraction comprising at least about 5% of the formulation by weight, wherein the particles of the small particle fraction have a d50 of less than about 5 μm.

14. The composition of claim 13, wherein the small particle fraction comprises calcium carbonate, silica or a combination thereof.

15. The composition of claim 13, wherein the small particle fraction comprises calcium carbonate.

16. The composition of claim 1, further comprising an anionic surfactant.

17. The composition of claim 16, wherein the anionic surfactant comprises sodium lauryl sulfate.

18. The composition of claim 1, further comprising a fluoride ion source.

19. The composition of claim 18, wherein the fluoride ion source is selected from stannous fluoride, sodium fluoride, potassium fluoride, sodium monofluorophosphate, sodium fluorosilicate, ammonium fluorosilicate, amine fluoride, ammonium fluoride, and a combination of two or more thereof.

20. The composition of claim 18, wherein the fluoride ion source comprises sodium monofluorophosphate.

21. A method of treating or preventing dental caries, comprising administering a composition according to claim 1 to the oral cavity of a subject in need thereof.

* * * * *